(12) United States Patent
Hickle

(10) Patent No.: US 10,058,117 B2
(45) Date of Patent: Aug. 28, 2018

(54) DIETARY HEALTH FOOD COMPOSITION, PACKAGE AND METHOD OF USE

(76) Inventor: Randall Scott Hickle, Lubbock, TX (US)

(*) Notice: Subject to any disclaimer, the term of this patent is extended or adjusted under 35 U.S.C. 154(b) by 417 days.

(21) Appl. No.: 12/927,590

(22) Filed: Nov. 18, 2010

(65) Prior Publication Data
US 2011/0123506 A1    May 26, 2011

Related U.S. Application Data

(60) Provisional application No. 61/281,845, filed on Nov. 23, 2009.

(51) Int. Cl.
*A61K 38/43* (2006.01)
*A23L 33/17* (2016.01)
*A23L 33/115* (2016.01)
*A61P 3/04* (2006.01)
*A23L 33/00* (2016.01)
*A61K 38/00* (2006.01)

(52) U.S. Cl.
CPC ............ *A23L 33/17* (2016.08); *A23L 33/115* (2016.08); *A23L 33/30* (2016.08); *A23L 33/40* (2016.08); *A61K 38/00* (2013.01)

(58) Field of Classification Search
CPC ........ A23L 33/30; A23L 33/17; A23L 33/115; A23L 33/40; A61K 38/00
USPC ....... 424/94.1; 426/2, 601, 613; 514/1.1, 4.8
See application file for complete search history.

(56) References Cited

U.S. PATENT DOCUMENTS

| | | |
|---|---|---|
| 5,336,486 A | 8/1994 | Acharya |
| 5,605,893 A | 2/1997 | Kaufman |
| 5,843,921 A | 12/1998 | Kaufman |
| 5,855,949 A | 1/1999 | McLean |
| 6,339,076 B1 | 1/2002 | Kaufman |
| 6,534,487 B1 | 3/2003 | Kaufman |
| 6,905,702 B1 | 6/2005 | Kaufman |
| 7,025,984 B1 | 4/2006 | Jandacek et al. |
| 2005/0014111 A1 | 1/2005 | Matson |

(Continued)

FOREIGN PATENT DOCUMENTS

NL    WO 2009131436 A1 * 10/2009 ............... A23C 3/02

OTHER PUBLICATIONS

Lyly et al. The FASEB Journal www.fasebj.org Apr. 2009 The FASEB Journal vol. 23 No. 1 Supplement 101.4 (abstract).*

*Primary Examiner* — Subbalakshmi Prakash
(74) *Attorney, Agent, or Firm* — Dorsey L. Baker

(57) ABSTRACT

A safe and effective dietary composition and method of use in which the composition contains protein, fat and carbohydrates in ratio of approximately 33% protein, 60% fat and 8% carbohydrates, the fat preferably being monounsaturated (MUFA) and polyunsaturated (PUFA) and providing, preferably, less than 800 calories per day. The preferred method of use includes consumption of a small quantity of this composition on an hourly basis which, preferably, is divided into some 16 equal dosages for the purpose of maintaining a continuous presence of macronutrients in the gastrointestinal tract to stimulate the production of hormones that produce feelings of satiety, a sense of well being and that suppress sensations such as hunger. In addition to this composition and the preferred method of consumption, the dieter may also consume salads that, preferably, provide no more than 250 calories.

9 Claims, 2 Drawing Sheets

(56) References Cited

U.S. PATENT DOCUMENTS

| | | |
|---|---|---|
| 2005/0214362 A1 | 9/2005 | Peyman |
| 2006/0105093 A1* | 5/2006 | Bialek et al. ................. 426/604 |
| 2006/0287384 A1* | 12/2006 | Behnam ........................ 514/440 |
| 2007/0269561 A1 | 11/2007 | Hudson |
| 2008/0081840 A1* | 4/2008 | Myers et al. ................. 514/558 |
| 2009/0011074 A1 | 1/2009 | Bialek et al. |
| 2009/0062231 A1 | 3/2009 | O'Mara et al. |

* cited by examiner

DIETARY HEALTH FOOD COMPOSITION, PACKAGE AND METHOD OF USE

CROSS REFERENCE TO EARLIER FILED APPLICATION UNDER 35 U.S.C. §119(E)

This application is based upon and claims priority and other benefits from U.S. Provisional Patent Application Ser. No. 61/281,845 filed Nov. 23, 2009.

FIELD OF INVENTION

These inventions relate to a dietary composition and method that effectively assists personal weight loss and prevents weight gain while substantially suppressing the individual's appetite and hunger pangs and promoting a global sense of well being. These inventions also relate to healthy food supplements that will ameliorate individual health problems such as atherosclerosis, inflammatory syndromes such as arthritis, and diabetes. When desired, the present inventions may provide long term health enhancement through, for example, body exchange of saturated and trans-isomer fatty acids with unsaturated and cis-isomer fatty acids in what is termed total body rehabilitation. Finally, the inventions of this disclosure are related to methods of consumption of these dietary nutrients and healthy nutritional supplements that render their physiological and hormonal results to be substantially more effective in appetite suppression, weight reduction, and sense of well being, while mitigating symptoms and progression of diseases such as inflammatory syndromes like arthritis and atherosclerosis.

THE PRIOR ART

For years, individuals and the health industry have sought to prevent weight gain and to effect weight loss, thus avoiding the co-morbidities associated with obesity such as insulin resistance, diabetes, atherosclerosis, high blood pressure, dyslipidemias, sleep apnea, degenerative joint disease and pain syndromes. Numerous efforts, many of which are at least partially successful, have been utilized. For example, the Atkins™ diet, formulated by Dr. Robert C. Atkins, M.D. has served many persons well in their weight loss efforts and, on belief, in the enhancement of one's overall health. For instance, Dr. Atkins has asserted that many have not only lost weight, but in addition have minimized risk of atherosclerosis and of Type II diabetes. (See his book, "Atkins Diabetes Revolution", published by HarperCollins Publishers, Inc., 2004.)

The Adkins™ diet focuses upon consumption of protein and fat while recommending a minimum quantity of carbohydrates. In addition to his diet, an associated company, Atkins Nutritionals, Inc. of Denver, Colo. has sold supplemental food products such as shakes and bars. These products exhibit the same focus on a high fat-high protein diet and are used to supplement the individual's diet, or, in some cases, are used as a substitute for dieter's meals. The Atkins™ diet, being high in fat, has been criticized by many as unhealthy. Moreover, this diet does impose burdens of dietary planning, calorie counting, and is not believed to have sufficient appetite suppression which renders its use difficult for some.

Another popular diet comes from NutriSystems™ which is believed to provide the dieter with prepackaged foods for all of the dieter's meals. This diet is said to permit more carbohydrates than the Atkins™ diet and it focuses on foods with a low glycemic index that are said to minimize the dieter's production of insulin. While such prepackaged foods are believed to be convenient to the dieter and minimize the necessity to count calories and the time in planning and preparing meals, the NutriSystem has been criticized as expensive and lacking tastefulness and palatability. The medical literature suggests that NutriSystem along with many other dietary systems work to some extent, but that many participants find it difficult to maintain compliance for a sufficient period of time to achieve their optimal weight target. NutriSystem is not believed to adequately suppress hunger nor promote a general sense of well being which renders its use difficult for sufficiently long periods of time for some.

Weight Watchers™ is another dietary concept in which members pay a fee to attend meetings and to obtain information about foods and dieting. This organization is known to sell some prepackage foods, but its focus is upon member support at meetings, and on the use of a counting system that assigns points to each food consumed by the dieter. The program stresses the importance of meeting goals with respect to the number of points (calories) consumed. Again this system requires continual planning, calculations and record keeping by the dieter.

Another dietary advisement, commonly known as ELMO and apparently named for the character Elmo of Sesame Street suggests that to lose weight, one should Eat Less More Often. As understood, this diet suggests eating smaller quantities of food more often. On belief, the diet advocates eating small portions of food every three or four hours. The dieter still has to select and prepare the food. Many find it difficult to select, purchase and/or prepare small food preparations. Further, the ELMO diet is not associated with teaching of methods to minimize hunger and promote a sense of well being by selection of the appropriate nutrients.

It is believed that with any of these diet systems, caloric restriction sufficient for weight reduction or prevention of weight gain can be obtained. However, the growing epidemic of obesity indicates that many find it difficult to sustain diligent execution of these nutritional guides and systems for the extended period of time required to reach an optimal target. It is believed one of the principal reasons for this difficulty is these dietary systems, when applied as directed, cause many to be in a "dieter's mood", to be irritable, grumpy, dissatisfied, and/or ill-at-ease—resulting in a mental state herein defined as a lack of a general sense of well being. Additional calorie consumption often immediately improves their mood; however, this dietary noncompliance defeats the dieter's intent and the effectiveness of these diets. Thus, a large segment of the population continues to seek a method and system of calorie and nutrient management that allows them to sustain participation in a dietary system for a sufficient period of time to achieve optimal targets. This continued effort to find a solution is mandated by our nationally recognized problem of overweight and obesity that continues to exacerbate. And this continued exacerbation is well described in the SUMMARY of the weekly report entitled "Morbidity and Mortality Weekly Report" of the Centers for Disease Control and Prevention of Jul. 24, 2009 (Vol. 58/No. RR7). It states:

Approximately two thirds of U.S. adults and one fifth of U.S. children are obese or overweight. During 1980-2004, obesity prevalence among U.S. adults doubled, and recent data indicate an estimated 33% of U.S. adults are overweight (body mass index [BMI] 25.0-29.9), 34% are obese (BMI≥30.0), including nearly 6% who are extremely obese (BMI≤40.0). The prevalence of being overweight among children and adolescents increased substantially during 1999-2004, and approximately 17% of U.S. children and adolescents are overweight (defined as at or above the 95% percentile of the sex-specific BMI for age growth charts). Being either obese or overweight increases the risk for many chronic diseases (e.g., heart disease, type 2 diabetes, certain cancers, and stroke).

The inventions of this application are submitted to be a very substantial, and effective, but simple and straightforward answer to this recognized, exacerbating problem of obesity and the resulting health problems facing this country.

SUMMARY OF INVENTION

On belief, the present inventions constitute important, healthy, affordable choices in nutrition efforts to not only control but to reverse obesity and overweight conditions. Indeed, these inventions overcome the complexity of prior known dietary concepts, provide very convenient and low cost dietary food substances that deliver safe and effective weight management, appetite suppression with a global sense of well being, and health enhancement—all without imposing complex dietary decisions or calorie counting upon the individual.

These dietary compositions and their methods of use are premised, not upon calorie counting, but upon a novel approach of using physiological factors to control hunger and to provide satiety. Indeed, the inventions presented herein comprise dietary compositions that utilize physiological factors of hormones, neurotransmitters, gastric motility and other physiological factors to provide 1) satiety and 2) to minimize hunger thereby reducing the dieter's need for substantial willpower during the diet. On belief, such is achieved, in large part, by the composition and method that, by reason of physiological factors, continuously sustains the presence of certain nutrients in the gastrointestinal tract—while simultaneously providing a restricted calorie consumption that compels weight management and/or weight loss—this with a very palatable, dietary food composition and method of consumption.

The preferred embodiments of my inventions comprise a simple dietary composition consisting primarily of protein, and fats (preferably monounsaturated fats (MUFA) and polyunsaturated fats (PUFA)). In its most preferred current form, the diet comprises a single dietary food substance formed primarily of egg whites for protein, unsaturated fat in liquid form and flavoring to be consumed at a rate of approximated 1 pint per day, the dietary substance being consumed at regular intervals, preferably hourly, throughout the day. The preferred embodiment provides satiety even though consumption does not exceed approximately 750 calories per day—a quantity well below the quantity (2000 or more) used by most individuals on a daily basis. The result is weight loss! A small quantity of carbohydrates may be added to this composition for flavor and, on belief, for some hormonally mediated gastrointestinal responses to carbohydrates during times of caloric restriction. The food composition may include vitamins, minerals fiber from sources such as psyllium husk and other desirable health food additives, but preferably such additives will not affect or add substantially to the calories provided by the primary macronutrient ingredients of protein, fat and carbohydrates. Flavoring is also added to render the composition more palatable. In addition to this food consumption of approximated 750 calories per day, the diet may include a simple salad such as that currently offered by McDonalds Franchises so as to add an additional 250 calories per day to constitute the dieter's primary source of carbohydrates and fiber. In an alternative embodiment, dietary fiber and, preferably, low glycemic index carbohydrates can be directly included as supplements in the diets.

The effectiveness of this composition in weight management and weight loss results, in part, from discoveries that this composition will have physiological effects on hormones, neurotransmitters and gastric motility so as to avoid hunger desires and maintain satiety.

Finally, this inventor has further discovered that the time period of such feelings of absence of hunger, satiety and a sense of well being can be continuously maintained by repeated, continued consumption or dosage of his dietary compositions.

Accordingly, these inventions are intended to provide and achieve, among other things, one or more of the following goals and objectives:

1) To provide a simple, convenient and healthy dietary composition of standard, available food substances that enables individuals to maintain total daily energy consumption at a level well below 2000 calories with a satiety-induced sense of well being and without the discomfort of hunger, without the problems of dietary food selection and preparation and without the inconvenience and time cost of calorie counting and dietary manipulation;

2) To provide a very simple diet composition having a low cost formulation that is palatable, easy to produce, comprising controlled doses of primarily readily available ingredients of fats, proteins and carbohydrates specially selected to induce satiety, substantial appetite suppression, weight management and weight loss;

3) To provide a safe and effective dietary concept, substance and method that that may be consumed on a regular basis to avoid sensations of hunger while maintaining a continuous state of satiety, a sense of wellbeing and the presence of nutrients in the gastrointestinal tract;

4) To provide diet compositions that may be formulated of selected mono and poly unsaturated fats that have notable health enhancement qualities and that include among other things, anti-inflammatory effects, reduction in pain, protection against heart disease, enhancement of the circulatory systems, reduction of high blood pressure and type II diabetes and arthritic conditions;

5) To provide dietary compositions with dosed portions of the macronutrients protein and fat and carbohydrates to which may be added fiber, vitamins, healthy enzymes such as Q-10, and/or minerals without adversely affecting the appetite suppression features of the dietary food composition or its total calorie count;

6) To provide a dietary composition that utilizes natural phenomena and physiological factors to assist in continuously sustaining the presence of nutrients in the gastrointestinal tract;

7) To enhance satiety and/or a sense of well being using natural phenomena by providing a dietary composition primarily of fat and protein with lesser amounts of carbohydrates to induce the body to enhance its production of the satiety hormone cholecystokinin (CCK), a protein that is released by I cells in the lining of the gastrointestinal tract, to control (and delay) the emptying of the stomach;

8) To enhance satiety and/or a sense of well being using natural phenomena by providing a dietary composition primarily of fat and protein with lesser amounts of carbohydrates to induce the body to minimize its production of the hunger hormone Grehlin by P/D1 cells principally in the gastrointestinal lining of the stomach that results in desires of hunger;

9) To enhance satiety and/or avoid desires of hunger by providing a dietary composition that enhances the production of Peptide YY (PYY), a protein that is released by L cells in the lining of segments of the gastrointestinal tract including the esophagus, stomach, duodenum and ileum and the colon;

10) To enhance satiety and/or delay gastric emptying through natural phenomena by providing a dietary composition that continuously stimulates the secretion of the satiety hormone Glucagon-like peptide-1 (GLP-1) from L cells lining the intestine;

11) To increase levels of Secretin secretion from S-cells principally in the duodenum thereby causing a delay in gastric emptying;

12) To increase levels of Gastric Inhibitory Peptide secretion from K-cells principally in the duodenum and jejunum thereby causing a delay in gastric emptying and decreased gastrointestinal motility;

13) To increase levels of Enteroglucagon secretion from L-cells principally in the ileum and colon thereby causing a delay in gastric emptying;

14) To increase the levels of Pancreatic Polypeptide secretion from PP cells in the pancreas thereby causing a reduction in appetite and decreased gastrointestinal motility;

15) To increase the levels of Amylin secretion from Beta cells in the pancreas thereby causing a delay in gastric emptying;

16) To increase the levels of Oxyntomodulin release from L-cells principally in the ileum and colon thereby causing a reduction in appetite and a delay in gastric emptying;

17) To increase the levels of Gastrin release from G-cells principally in the stomach and duodenum thereby causing increased contraction of the pyloric valve and a delay in gastric emptying;

18) To decrease the levels of Motilin release from M-cells principally in the duodenum and jejunum thereby decreasing gastrointestinal motility;

19) To decrease the levels of Vasoactive Intestinal Peptide (VIP) release as a neurotransmitter thereby causing decreased gastrointestinal motility and increased tone in the pyloric sphincter;

20) To enhance weight loss by providing a dietary composition that enhances the production of glucagon to release triglycerides from adipose cells for use in the production of energy and to minimize the production of insulin that promotes the storage of triglycerides in adipocytes (fat cells);

21) To provide a dietary composition that can achieve a substantial exchange of saturated fat and undesirable forms and amounts of unsaturated fat of the dieter to desirable forms and ratios of fats that may have, among other benefits, anti-inflammatory effects with a view of rehabilitating or enhancing the well being of the body;

22) To provide a dietary composition that may also include the use of saturated fats together with protein;

23) To provide a dietary composition that may contain selective additives to further address health problems such as atherosclerosis, diabetes, harmful lipid profiles, and possibly avoid bariatric surgery, etc.; and 24) To provide methods of consumption of dietary compositions that will enhance sustaining macronutrients in the gastrointestinal tract over time and will further stimulate the production of certain hormones consistently throughout the day.

DESCRIPTION OF THE DRAWINGS

The manner in which these and other objects of my invention are achieved is disclosed in the following detail description and drawings in which.

DETAIL DESCRIPTION

Figure 1:
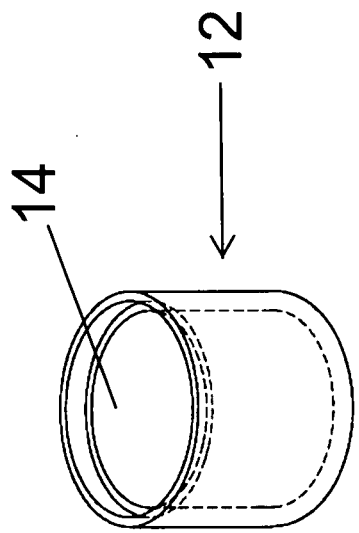
FIG. 1 is a perspective view of a preferred embodiment of a container having a measuring cap for packaging the dietary composition of the instant inventions and for measuring the consumptive quantity of the composition for consumption on an intermittent basis.
Figure 1:
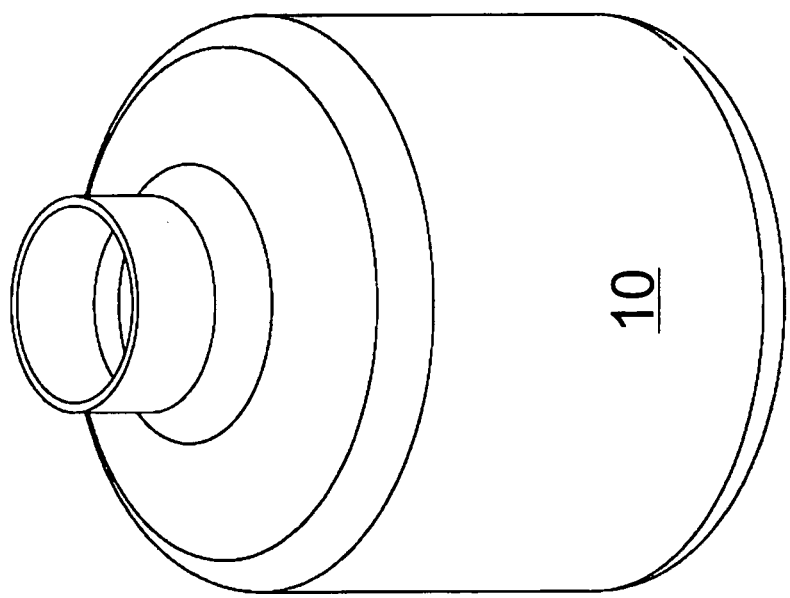

As noted above, a principal goal and objective of this invention is to provide a simple, healthy dietary composition of standard, available food substances that minimizes hunger and provides satiety to enables individuals to maintain a dietary status at a level well below 2000 calories with satiety, with a sense of well being, and without the discomfort of hunger. This inventor has discovered that such can be achieved through a specially selected dietary composition that has certain physiological effects within the gastrointestinal tract—effects that are important in achieving effective weight management and improved health while maintaining the individual's satiety, comfort and sense of well being. Importantly, this inventor has further discovered that such effects can be enhanced by multiple, periodic servings of the dietary formulation throughout the day so as to continuously maintain nutrients in the gastrointestinal tract and to avoid feelings of hunger that may cause the dieter to terminate the physiological state of ongoing lipolysis.

The dietary method and composition disclosed herein are premised on the inventor's belief of the existence of an integrated enteroendocrine axis system that effectively regulates the body's response to traditional methods of caloric restriction. Thus, this enteroendocrine axis is one of the predominant control systems for regulation of food intake. Identification of this enteroendocrine axis control system as a central feature of caloric intake regulation has profound implications for design and development of successful weight loss programs.

Formulation of a control system paradigm for the enteroendocrine axis that prevents long term successful caloric restriction (i.e., dieting) is premised on the inventor's belief that the lining of the entire gastrointestinal tract, from the mouth, continuing through the esophagus, stomach, duodenum, jejunum, ileum, colon and rectum is embedded with thousands of specialized cells. For the most part, each of these individual enteroendocrine cells "acts alone"; that is, in general, the individual cells are not neurologically controlled at conscious or subconscious levels of the central nervous system. Instead, each individual cells merely monitors its environment for the presence of one or more of the macronutrients, protein, carbohydrate, or lipid. When these macronutrients (in original form or partially digested and mixed with other substances) are present immediately at the site of a cell's receptors in the gastrointestinal tract lining, the specialized cell is in a "fed" state. When the macronutrients a particular cell monitors are absent, this cell switches to an "unfed" state. For descriptive purposes, the inventor uses two broad categories to describe these specialized cells "satiety signaler cells" that send messages of macronutrient presence, and "starvation signaler cells" that send messages communicating the lack of macronutrients in the lumen of the gastrointestinal tract. The matrix in Table 1 describes these cell categories and their response in each state.

TABLE 1

Enteroendocrine Cell Types And States

| | Fed State | Unfed State |
| --- | --- | --- |
| Satiety Signaler Cells | Start production and secretion of hormonal messages locally and into the circulating blood, thereby sending circulating messages to the entire body signaling the condition of nutrient sufficiency | Stop production and secretion of hormonal messages locally and into the circulating blood, thereby removing from the entire body signals of nutrient sufficiency |
| Starvation Signaler Cells | Stop production and secretion of hormonal messages locally and into the circulation that signal the condition of nutrient insufficiency | Start production and secretion of hormonal messages locally and into the circulation that signal the condition of nutrient insufficiency |

Although each enteroendocrine cell generally acts alone, they collectively act as an integrated serial array that senses the presence of nutrients throughout the entire length of the gastrointestinal tract, signaling and directing the body's powerful response to traditional methods and nutrient compositions taught for caloric restriction. Some of the hormonal signals trigger a local response within a short distance from the cell (paracrine effect) while other responses are triggered at sites far from the cell that produced the hormonal signal (endocrine effect). Because these hormonal messages are released into the general circulation, they communicate their endocrine signals to many organs throughout the body, and these organs in turn amplify the signals or otherwise respond to the message. Some of the hormonal signals trigger neurological responses that further amplify and coordinate the body's response to the macronutrient state in the lumen of the gastrointestinal tract. Neurological responses may involve local reflexes that, for example, control the tone of gastrointestinal sphincters. Other neurological responses are centrally mediated via the parasympathetic nervous system (e.g., the vagal nerve) and the sympathetic nervous system. Ultimately, the body's response to caloric restriction is shaped by the summation and subsequent amplification of signals received from many thousands of enteroendocrine cells embedded in the lining of the gastrointestinal tract. As a system, in the whole, enteroendocrine cells comprise an integrated network that tightly regulates the continued intake of nutrients and defeats haphazard attempts at caloric restriction. When dieters attempt to restrict calories without making accommodations for the power and control of this enteroendocrine axis, they suffer the consequences and find themselves unable to exert willpower over their body's hormonal state. An understanding of the physiological effects of the inventor's dietary compositions on these enteroendocrine cells and their hormonal signal effects is believed to be important to an understanding of the scope of the inventions disclosed herein and to the various modifications that are within the scope of the inventions disclosed and claimed herein.

These physiological effects resulting from the consumption of the dietary compositions react with enteroendocrine cell types, with certain glands and with neurotransmitters to ultimately provide satiety, to eliminate hunger and to reduce the motility of nutrients within the gastrointestinal tract. These cell types, glands and neurotransmitters will be summarily described together with their effect of dietary composition on them.

First, it is known that the P/D1 cells embedded in the gastrointestinal tract lining the fundus of the human stomach together with the epsilon cells of the pancreas produce Grehlin the hormone that results in hunger. A second effect of Grehlin is to increase gastrointestinal motility that accelerates the passage of nutrients through the gastrointestinal tract. Production of this hormone is stimulated by the absence of nutrients in the stomach and consequently, these inventions seek to minimize the production and the effect of Grehlin by maintaining nutrients (primarily fats and protein) in the stomach.

Motilin is a second hormone associated with fasting (i.e., the absence of macronutrients in the lumen of the gastrointestinal tract). Produced by M-cells located principally in the duodenum and jejunum, this hormone also increases gastrointestinal motility and among other effects, accelerates the clearance of nutrients from the immediate environment of P/D1 cells in the fundus of the stomach, thereby resulting in hunger. Again, the dietary compositions disclosed herein seek to reduce gastrointestinal motility and to minimize the feelings of hunger even while maintaining restriction of caloric intake.

Vasoactive Intestinal Peptide, a neurotransmitter rather than a hormone, is a third messenger molecule associated with the absence of macronutrients in the gastrointestinal tract. Released from nerve endings throughout the gastrointestinal tract during periods of fasting, this neurotransmitter relaxes the pyloric sphincter valve thereby increasing exit of food from the stomach and also increases gastrointestinal motility, thereby accelerating the clearance of nutrients from the immediate environment of P/D1 cells in the fundus of the stomach, and thus increasing production of Grehlin and the associated sensation of hunger.

The present dietary compositions of these inventions not only reduce levels of hormones that increase gastrointestinal motility and the feeling of hunger, the compositions also act on other enteroendocrine cell types to cause increased levels of hormones that cause feelings of 1) satiety and 2) reduced gastrointestinal motility. Thereby, these dietary compositions prolong the presence of nutrients in the stomach and other segments of the intestine so as to prolong the absence of hunger and the feeling of satiety.

One of those hormones is cholecystokinin (CCK), a satiety hormone that is synthesized and secreted into the blood by I-cells in the lining of the duodenum and jejunum segments of the small intestine. Production of CCK is stimulated by fat or protein rich chyme, the semisolid partially digested food expelled by peristaltic action from the stomach through a relaxed pyloric valve into the duodenum. CCK inhibits emptying of the stomach in part by decreasing peristaltic activity and in part by causing the pyloric valve to contract thus prolonging the presence of nutrients in the stomach at the site of the P/D1 class of enteroendocrine cells and thereby maintaining them in a "fed" state and diminishing their secretion of Grehlin into the circulation. As noted, the presence of nutrients in the stomach is known to suppress the production and secretion into the circulation of the hunger hormone, Grehlin, from P/D1 cells in the lining of the stomach. Thus, CCK assists to generally decrease peristaltic forces in the stomach and small intestine that forward propel food in the gastrointestinal tract thus prolonging the presence of nutrients in the intestine and thereby prolonging the enteroendocrine axis of cells in a "fed" state by extending the duration of the presence of fat and protein and carbohydrates in the stomach and in the small intestine. In addition, it is believed that circulating levels of CCK have a direct effect on the central nervous system producing a sensation of satiety and an associated sense of well being. Consequently, these dietary inventions comprise convenient pre-prepared, caloric portions of fat and protein in one's diet that produce feelings of satiety, and of well being, and in addition, such results in an extended presence of these macronutrients in the duodenum and jejunum to further extend the feelings of satiety and well-being—while simultaneously suppressing the production of Grehlin, VIP, and Motilin.

Peptide YY (PYY) is another hormone that creates satiety and decreases gastrointestinal motility. It is produced by the L-cell class of enteroendocrine secretory cells lining the intestine primarily in the ileum and the colon. Additionally, about 10% of PYY is secreted from cells lining the esophagus, stomach, duodenum and jejunum. The presence of protein in the immediate environment of L-cells lining the intestine is believed to result in an increase in PYY, and consequently, in the degree of satiety experienced by a dieter.

Glucagon-like peptide-1 (GLP-1) is another hormone that creates satiety and is, also produced and secreted from L-cells lining the intestine. GLP-1 decreases peristaltic activity in the stomach thereby slowing gastric emptying and increases satiety and reduction in food intake. The natural secretagogues (agents that stimulate secretion) for GLP-1 from L-cells include threshold chyme concentrations of the macronutrients: lipid, protein, and carbohydrate. The kinetics of GLP-1 highlight the precise timing of this enteroendocrine control system. After intake of macronutrients, GLP-1 is rapidly released, but once in the circulation, it is also rapidly degraded by a circulating enzyme and has a half life less than 2 minutes. Because the biological effects of GLP-1 are short lived and rapidly reversible, it is not merely the total amount of GLP-1 secretagogue macronutrients per day that matters, but rather it appears it is an instantaneous concentration of these macronutrients dynamically present in chyme throughout the entire day that determines blood concentrations of GLP-1, providing a central element of control for food intake. In summary, in response to the presence of threshold concentrations of macronutrients in the chyme, L-cells produce and secrete short-lived GLP-1 into the circulation. Thus, for GLP-1 to maintain a reduction in appetite and delayed gastric emptying, thereby prolonging the presence of nutrients in the stomach (prolonging a sense of fullness and a decrease in production of the hunger hormone, Grehlin, while maintaining calorie restricted intake of food) and a satiety-induced sense of well being is further promoted by the sustained and continuous presence of threshold concentrations of macronutrients in the chyme.

Gastrin is a hormone associated with macronutrient presence. Produced by G cells principally in the pyloric antrum and duodenum in response to protein and gastric distension (e.g., from consumption of macronutrients, water, and fiber), gastrin stimulates production of stomach acid and delayed gastric emptying.

Secretin is a hormone that also causes delayed gastric emptying. Acidic (low pH chyme) exiting the pyloric valve stimulates S-cells located principally in the duodenum to secrete Secretin, thereby slowing gastric emptying until the pH of the acidic chyme in the duodenum is neutralized. Thus, in a two step process, consumption of macronutrients, water, and fiber increases levels of Gastrin that cause acid production thereby lowering pH in chyme. Acidic chyme, when exiting the stomach, activates S-cell Secretin secretion which lowers the rate of gastric emptying.

Gastric Inhibitory Peptide (GIP) has effects similar to Secretin. Produced by K-cells in the duodenum and jejunum in response to low pH chyme, GIP delays gastric emptying and decreases gastrointestinal motility.

Enteroglucagon, produced in response to lipid and carbohydrates by L-cells in the ileum and colon, causes delayed gastric emptying.

Oxyntomodulin is a satiety hormone also produced by L-cells in the colon and ileum in response to carbohydrates, lipids, and protein that causes satiety and delayed gastric emptying.

Pancreatic Polypeptide (PP) is produced by PP-cells in the pancreas in response to the presence of protein in the intestinal lumen causing satiety and decreased gastrointestinal motility.

Amylin is produced and secreted from pancreatic beta cells in response to blood glucose and causes delayed gastric emptying.

On belief, maintaining the sustained presence of macronutrients in chyme with dosed intake of calorie-restricted macronutrients is one of the central and controlling elements of maintaining appetite suppression and a satiety hormone-induced sense of well being during sustained maintenance of calorie restricted diets. The central and controlling element of continuously managing the threshold concentrations of calorie restricted macronutrients in chyme has not been previously appreciated in nonsurgical prior art weight management systems.

In the inventor's view, the present inventions best utilize the profound and controlling effects of the satiety hormones CCK, PYY, GLP-1, Secretin, GIP, Enteroglucagon, PP, Amylin, Oxyntomodulin, and Gastrin by selecting a palatable dietary composition comprised primarily of fat and protein with lesser amounts of carbohydrates to maintain the presence of these macronutrients in the chyme of the gastrointestinal tract, thereby bathing the satiety enteroendocrine cells 1) to enhance their production and the resulting feeling of satiety, 2) to use these hormones to delay gastric emptying and intestinal peristalsis to maintain the calorie restricted doses of fat, protein, and carbohydrate in the stomach and small intestine as long as possible, and 3) to sustain the daily consumption of the dietary composition in amounts less than 2000 calories per day while feeling the effects of satiety and avoiding the production of the hunger hormone, Grehlin, and the intestinal motility enhancing signals, VIP and Motilin, throughout the day.

The dietary composition to be described is believed to work very effectively to stimulate release of CCK, PYY, GLP-1, Secretin, GIP, Enteroglucagon, PP, Amylin, Oxyntomodulin, and/or Gastrin and to inhibit Grehlin, Motilin, and VIP to simultaneously induce satiety and restrain hunger sufficient to enable the dieter to stay on the calorie restricted diet proposed herein. The intestinal tract contains many other enteroendocrine cells secreting hormones and has cell receptors that are acted upon by hormones including somotostatin. While their full effects on hunger and satiety are not known in detail, it is the inventor's present conclusion that they do not interfere with or have an adverse effect upon and are likely to enhance the effectiveness of the dietary composition and its method of use as further described herein and the resulting feelings of satiety and absence of hunger.

As noted above, the presently preferred dietary composition of my invention is comprised primarily of fat and of protein and lesser amounts of carbohydrates. The preferred fats are monounsaturated fats (MUFA) and polyunsaturated fats (PUFA). In its most preferred form at this time, the diet comprises a simple dietary liquid food substance formed primarily of egg whites for protein and unsaturated fat together with 50 calories of carbohydrate and flavoring to be consumed at a rate of approximately 18 oz per day in hourly intervals. The preferred list and quantity of ingredients with chocolate flavoring is:

| Ingredient | Quantity | Calories | Daily Servings |
|---|---|---|---|
| Egg White, Pasteurized | 16 oz, 1 pint | 250 | Grams Protein = 50 |
| Extra Virgin Olive Oil | 3.3 TBSP, 1.65 oz | 396 | Grams Fat = 46.2 |
| Barlean's Fish Oil | .68 TBSP, 0.68 oz | 30.6 | Grams Fat = 9.18 |
| Barlean's Flax Seed Oil | 0.1 TBSP, 0.05 oz | 12 | Grams Fat = 1.4 |
| Nutiva Hemp Oil | 0.1 TBSP, 0.05 oz | 13 | Grams Fat = 1.4 |
| Whey | 0.125 TBSP, .02125 oz | 1.72 | Grams Protein = .43 |
| Hershey's Cocoa | 1 TBSP | 10 | Grams Carb = 3 Grams Fat = .05 |
| Hershey's Chocolate Syrup | 1 TBSP | 50 | Grams Carb = 12 |
| Total Calories & Servings | | 763.32 | 16 |

As reflected by the table, the dietary composition provides only 763 calories to be consumed in sixteen equal portions during the day. Approximately one third of the calories are derived from protein, 60% from fat, and 8% from carbohydrates. These 763 calories from this chocolate flavored liquid diet composition are not only very palatable from the perspective of taste, but they are also sufficient to induce physiological effects that provide satiety and freedom from hunger.

In addition to essential fatty acids (fat) and amino acids (protein), carbohydrates, fiber, vitamins, and minerals, a dieter should also consume a sufficient quantity of water. Beyond the water in food, it is recommended that an average male should consume 96 ounces and a female 64 ounces of water. Dietary water supports digestion, food absorption, metabolism, and electrolyte balance. For the purposes of this invention, in combination with the nutrient composition herein described that prolongs the duration in the stomach of consumed solids and liquids, water can also aid in appetite suppression. On belief, some dieters don't consistently consume the same quantity of calories per day, but they are more consistent in consuming approximately the same weight of food each day. Water is a principal component of the weight of food. For example, the recommended 96 ounces of daily water for a male weighs 6 pounds and the female recommended 64 ounces weighs 4 pounds. On belief, the presence of stretch receptors in the stomach reduce the production of the Grehlin, the hunger hormone, when activated and the weight of food is more directly related to activation of these stretch receptors than caloric content. The inventor's preferred method is enhanced by the hourly consumption of approximately 6 ounces of water for males and 4 ounces for females. If the pyloric sphincter is maintained in a narrowed state and peristaltic activity diminished, thereby reducing the exit of chyme from the stomach, the weight of daily water consumption, particularly if combined with concurrent doses of water soluble fiber, will more effectively activate stretch receptors in the stomach lining. Maintaining the pyloric valve in a narrowed position and reducing the peristalsis of the stomach is best accomplished as previously described by elevating the satiety hormones, CCK, PYY, GLP-1, Secretin, GIP, Enteroglucagon, PP, Amylin, Oxyntomodulin, and Gastrin along with lowering the levels of Grehlin, VIP, and Motilin.

It should be noted that most if not all dieters would lose weight on this calorie intake of 763 calories per day, particularly when one considers that the average person uses at least 2000 calories per day. However, in addition to consumption of this diet, the inventor believes that additional carbohydrates in the form of one or two salads or vegetable servings should be taken daily—which should add not more than 250 calories. The inventor contemplates adding these additional, preferably low glycemic index carbohydrates, to the nutrient composition in some embodiments. Through this supplementation if a dieter adds 250 calories of carbohydrates then the ratios change to approximately 30% carbohydrates, 25% protein, and 45% fat. Similarly, a dieter should consider taking additional fiber daily such as 4 or more capsules of psyllium supplement along with other fiber supplements in accord with labels on the purchased package. Finally, vitamins may be taken in addition to this dietary composition, although the inventor also contemplates the possibility of adding both fiber and/or vitamins to the composition. Those skilled in the art will appreciate that various flavorings, such as those manufactured and sold under the trademark "DaVinci Gourmet™" will provide many desirable alternative flavors of the dietary composition—flavors such as French vanilla, pina colada, strawberry, etc.

As noted earlier, this dietary formulation, to be most effective, is consumed in a manner to further sustain the presence of fat and protein along with limited carbohydrates in the intestinal tract, particularly in the stomach and the small intestine throughout the day. Among others, effects of the sustained presence of fat and protein include: 1) a reduced but safe blood sugar level, 2) a low insulin level, 3) a low level of Grehlin, the hunger hormone, and 4) and a high level of glucagon which causes the body to convert stored glycogen into glucose and which further induces lipolysis to effect release of stored fat from adipocytes for use as energy, i.e., weight loss.

The above table and stated ingredients are preferred by the inventor. However, in view of the different reactions of different persons, the different needs of men and women, their different metabolism rates, etc. it is presently believed that the minimum effective dietary composition each day would include not less than 20 grams of protein, 5 grams of fat in a composition that has not more than 1750 calories, the composition to be taken in not less than 7 servings at regular intervals. To the extent that one desires to add carbohydrates, such additions would preferably be complex carbohydrates having a low glycemic index.

As noted above, the inventor's dietary composition alone has an effect of stimulating the production of certain hormones that, in turn, help sustain the presence of the macronutrients in the intestinal tract for a longer period of time. Importantly, these effects can be further enhanced by consuming the composition in small quantities on a regular, consistent basis. As shown in the above table for the preferred embodiment, the macronutrients can be divided into some 16 equal dosages and taken on an hourly basis. Such a scheduled consumption practice will further insure the continuous presence of macronutrients in the gastrointestinal tract and the continued production of the hormones that produce feelings of satiety, a sense of well being and the suppression of the hunger hormone, Grehlin, and suppression of the stimulants of gastrointestinal motility, VIP and Motilin.

This continuous consumption can be well assisted by proper packaging which may take many forms. Such packaging should include methods and packages providing safe preservation up to the point of consumption of accurately measured dosages at regular, preferably one hour, intervals throughout the day. For example, the invention can be delivered in a multi-compartment container that integrates an ice pack to maintain refrigerated temperatures for prolonged times after removal from a freezer or refrigerator.

A currently preferred method of packaging this dietary composition is the use of a container with a large measuring cap that will accurately measure the amount to be consumed each hour. A drawing of such is depicted in FIG. 1 which is a drawing of a container 10 sized and designed to contain approximately 18 ounces of the liquid composition that may be refrigerated or otherwise cooled throughout the day. The cap 12 is formed of a shell having a measuring insert 14 press-fit therein. Preferably, the measuring insert 14 is sized to contain one sixteenth of the contents of the 18 ounce container. Each hour, the dieter merely pours the liquid dietary composition in the cap 12 until the measuring insert 14 is filled and then consumes that amount.

Figure 2:
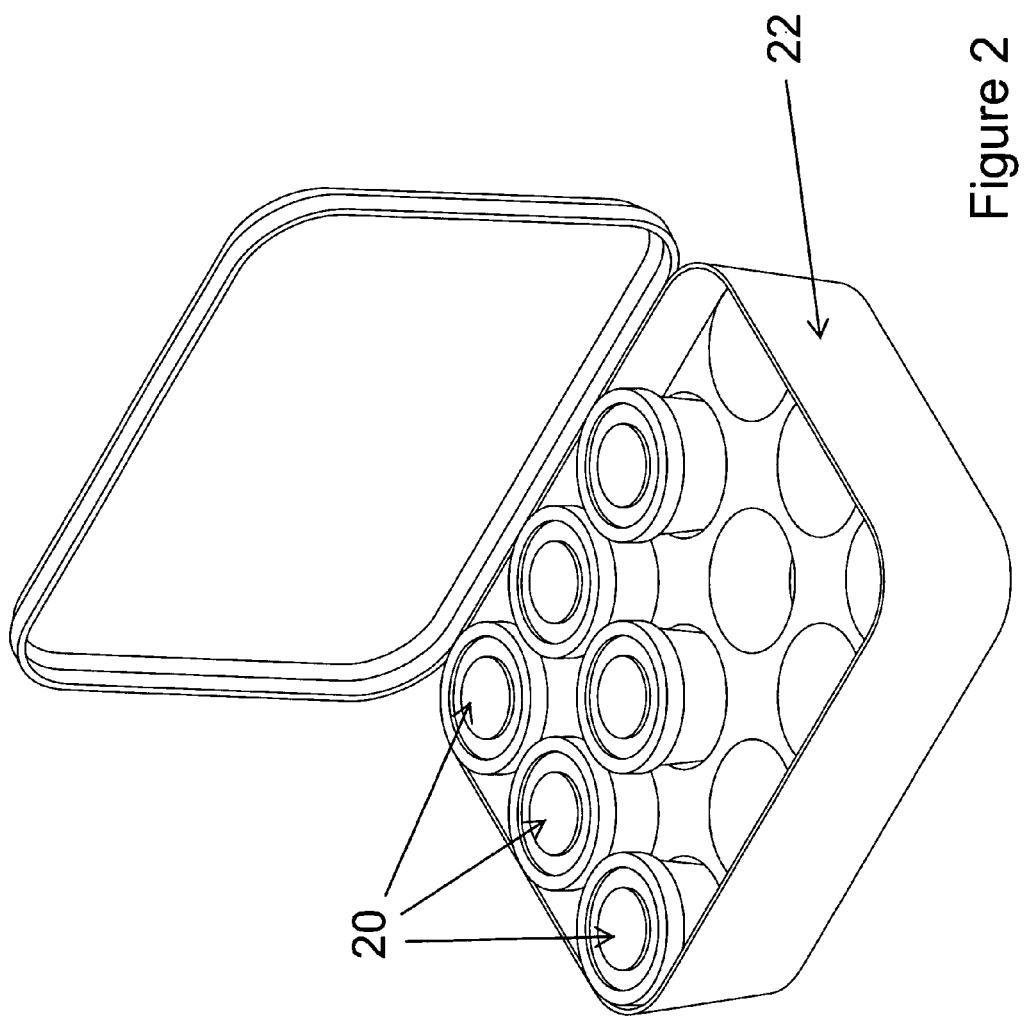
FIG. 2 is a perspective view of an alternative packaging system to facilitate multiple servings of the dietary food composition.

Another preferred method of packing this dietary composition is depicted in FIG. 2. Such comprises a plurality of small thermoformed plastic containers 20, each having a capacity of 1.125 ounces of dietary composition. A one day supply of the dietary containers may be placed in a larger tray like package 22 that may be refrigerated or cooled.

OTHER ALTERNATIVES, BENEFITS AND USES

The use of a conventional thermos container, not shown, having a measuring cap for each serving of dietary formulation is a third alternative that would facilitate the goal of sustaining fat and protein in the intestinal tract of the dieter. Indeed, such may be most helpful to those whose work environment precludes normal cooling and/or refrigeration and the thermos container would act as a substitute lunch box.

In light of the very palatable, tasteful alternatives, another alternative is to dilute the composition with water to create more volume, to package same in bottled or can containers, and sell them through refrigerated vending machines.

The inventor also believes that formulation of the product as a solid in a package such as a bar may serve as another alternative method of manufacture, sale and consumption. Indeed, it is believed that the formulation may also be integrated with solid substances that will release the macronutrients on a timely basis. In addition, the desired protein may take many forms in addition to that of egg whites. For example, the protein may be derived from fresh or reconstituted, freeze dried poultry and/or livestock products, and dairy products such as whey. The carbohydrates may be provided fresh or preserved by many available techniques including frozen, canned, dehydrated, or freeze dried. Finally, the dietary composition may be integrated into capsules and taken at regular intervals, and such may be particularly desirable when the ingredients are freeze dried or dehydrated. Time release of the nutrients can also be added to further enhance sustaining the macronutrients in the intestinal tract to achieve feelings of satiety and a sense of well being.

To date, a limited number of persons have successfully utilized this diet, as presently formulated to lose substantial weight. The benefits of this dietary composition, however, extend beyond weight loss. For example, formulations of targeted fatty acid composition such as omega-3 fatty acids from certain algae or fish are known to have substantial anti-inflammatory properties and are expected to have very beneficial effects upon patients with advanced atherosclerotic vascular disease at risk for morbid complications such as heart attack or stroke or who endure cardiovascular procedures such as stent placement or heart surgery, and the like. Many have recommended taking supplements of preferred fatty acids up to 4 grams per day to prevent or treat diseases such as atherosclerosis and inflammatory problems such as arthritis.

However, the inventor's nutrient composition and his method of continued consumption, when formulated with targeted optimal portions of preferential fatty acids is expected to have a greater impact on the dieter's stored fat, i.e., the dieter can expect to ultimately convert stored fat from triglyceride molecules and replace them with dietary fatty acids that are more anti-inflammatory. The inventor terms this total body rehabilitation. It is like an oil change—removing the old bad oil and replacing it with upgraded new oil. Moreover, this dietary composition has had a substantial effect on the inventor who consumed the formulation for a mere 21 days. Indeed, the change resulted not only in a substantial weight loss, but provided a significant, beneficial change in his lipid profile. That change is reflected in the following table:

|  | Prior to diet | After diet | Change |
| --- | --- | --- | --- |
| Total cholesterol | 149 | 128 | −21 |
| LDL cholesterol ("bad" cholesterol) | 89 | 65 | −24 |
| HDL cholesterol ("good" cholesterol) | 52 | 50 | −2 |
| Triglycerides | 76 | 51 | −25 |
| Fasting Blood Sugar | 119 | 112 | −7 |

Individuals skilled in the art will appreciate that further, numerous modifications and alternatives exist with respect to this dietary formulation—without departing from the scope of my inventions. For example, the formulation may be modified to be prescribed as a medical food to include such ingredients as 1) supplementation with vitamins such as B3 (niacin) at dosage levels sufficient to achieve lipid profile enhancement and reduction in vascular inflammation, and 2) a greater percentage of fish oil or other optimal fatty acids for the treatment of atherosclerosis and for patients who have endured vascular, cardiothoracic, heart surgery, procedures and the like. Moreover, as proffered, it is believed that the dietary composition will have a very salutatory effect on Type II diabetes as well as on other patients at a risk for atherosclerosis progression, and will further benefit from greater fish oil content with their fatty acids (EPA and DHA) and the like.

While MUFA and PUFA fats are preferred by the inventor, saturated fats can be acceptable. Indeed, saturated fats such as those of coconut oil and palm oil are believed to achieve the same enteroendocrine hormone effects, to provide satiety and/or to provide an excellent sense of well being and are reputed to have some beneficial effects such as raising HDL levels.

Those skilled in the art of weight management will also appreciate that the inventions disclosed herein have, at least in part, effects that are analogous to bariatric surgery and to an extent, this diet may, in some cases, constitute an alternative for that very expensive and un-pleasant surgery.

One of the main requirements for successful weight loss following bariatric surgery is strict adherence to a gastric by pass diet. Dietary recommendations include eating 2 to 3 small meals daily with disciplined avoidance of high-caloric snack foods between meals. Patients are directed to first consume essential nutrients including protein, vitamins, and minerals. This required strict compliance with these post-surgical dietary guidelines produces a significant change in the macronutrient composition of stomach contents.

This required strict compliance, in some cases, will be analogous to the change resulting for the diet compositions of the present inventions. Indeed, these inventions focus on limited quantities of the diet composition at timely intervals and the effect of such consumption is believed to produce a stomach chyme similar to that produced by the very restrictive diets of bariatric patients. Moreover, the inventor's diet when used as a substitute for bariatric surgery or as a specialty diet after bariatric surgery is expected to produce a similar chyme and will enhance the production of hormones such as CCK, PYY, GLP-1, Secretin, GIP, Enteroglucagon, PP, Amylin, Oxyntomodulin, and Gastrin to achieve satiety, a sense of well being and greater weight loss for the patient. Accordingly, it is believed that this diet will, in some cases, avoid the pain, scars, complications, cost, recovery time, complexities, and deleterious life-long metabolic alterations caused by the surgical consequences of bariatric surgery or alternatively, such will enhance post-bariatric surgery recovery and weight loss.

For many, the very act of dieting (restriction of calories) has a rebound effect of disinhibiting overconsumption behaviors. As described, one purpose of this invention is to avoid this normal "discomfort of dieting" by creating a consistent hormonal state with high satiety and low hunger in which a person is more capable of maintaining a prolonged restriction of consumed calories. In this physiological state, a person is more likely to be able to exert willpower. Beyond the creation of this consistent hormonal state, another enhancement of this invention is that of behavior modification that further improves the dietary formulation and the method of consumption.

In addition to this resilient physiological, hormonal, and psychological state characterized generally as "being in control", there are numerous additional social, environmental, psychological, and behavioral factors that contribute to caloric overconsumption despite known detrimental effects and despite an individual's contrary desires. Some of these factors are pathological in nature (e.g., bulimia). However, even in the absence of psychopathology, for many there are "addictive" foods that induce psychological pleasure and trigger loss of control and individuals become conditioned to compulsive caloric consumption of these foods. The term "addictive" in this context has been described by some as "conditioned hypereating" in distinction from addictions classically associated with physiological withdrawal syndromes to drugs such as heroin and alcohol. In popular terms, conditioned hypereating of addictive food is described as the "bet you can't eat just one" consumption of a single warm chocolate chip cookie that uncontrollably continues until the whole platter is gone. Conditioned hypereating is characterized by loss of control. It has been suggested that food science-optimized concentrations of fat, sugar, and salt contribute to the design of addictive foods which cause loss of control and conditioned responses resulting in powerful psychological attachments to pleasurable consumption routines despite a desire to avoid associated adverse consequences of caloric overconsumption. The addictive quality of a food is defined by the behavior of each individual in specific settings in response to that food. For one person, cheesecake with white wine in a pleasant restaurant may be a food that causes loss of control, but not for another.

Consequently, the invention described herein as a nutrient composition and method that creates a hormonal milieu enabling caloric restriction can be combined with a behavior modification program built, in part on protocols designed for successful management of other addictive substances such as alcohol and cocaine. To dampen continued powerful fixations on adverse repetitive behaviors, this behavior modification program implements protocols that simultaneously: 1) increase engagement in positive behaviors, 2) decrease activation of triggers (e.g., addictive foods, stressful situations, hyper-consumption social settings) that lead to loss of caloric consumption control.

The program allows participants to gain insight into their attitudes, but it ultimately achieves outcomes by altering behavior. Each participant is taught how to identify foods and settings and patterns of behavior that are associated with caloric over-consumption, and participants change behaviors associated with those foods and other stimuli that are potentially addictive for each individual. Behavior modification is built upon a rules-based approach, for example:

I don't take the first bite of that addictive food
I control my environment, keeping addictive foods out of sight, out of reach, not in my home.
I change routines that have caused me to over-consume foods that are addictive for me.
I don't eat food to make me feel better, so when I am sad, mad, or stressed, I find a non-food therapy.
I first focus on eating the things my body needs before considering addictive foods that merely please my palate.
I avoid social settings that condition my patterns of excess consumption.

Among other objectives, this biopsychosocial program improves management of difficult social settings, reduces stress triggers, enhances self esteem, improves knowledge of food nutrition, encourages community support groups, teaches reduction of exposure to and management of hyper-consumption cues, and trains participants in the development of consumption contingency plans.

Persons skilled in the art will appreciate the numerous variations and modifications that can be derived from and/or made according to the broad disclosure and scope of the numerous, beneficial inventions disclosed herein. All such derivations and modifications are intended to be within the scope of this patent and the claims attached or to be attached to the regular application to be filed on these inventions. Such derivations and modifications extend from the basic concept of weight loss, to satiety without hunger, to ameliorations of health problems such as atherosclerosis, diabetes, and arthritis, to total body rehabilitation with a very palatable food composition—while eliminating the present, time consuming concepts of calorie counting, food selection and preparation. Moreover, many of the variations and modifications within the skill of the art can be made without any deleterious effect upon the ability of these inventions to reduce blood sugar levels, lower insulin levels, and enhance levels of glucagon while elevating the satiety hormones, CCK, PYY, GLP-1, Secretin, GIP, Enteroglucagon, PP, Amylin, Oxyntomodulin, and Gastrin along with and the suppression of the hunger hormone, Grehlin, and suppression of the other stimulants of gastrointestinal motility, VIP and Motilin.

I claim:

1. A dietary composition for enabling safe, effective, convenient and low cost weight loss and/or management by an individual, with satiety and without imposing complex dietary decisions or calorie counting upon the individual, said composition comprising:
   a) a daily dietary composition of nutrients in which approximately 60% of the calories are derived from unsaturated fats and 30% are derived from protein;
   b) said composition being packaged to facilitate consumption in regular intervals throughout the day to continuously maintain nutrients in the gastrointestinal tract and to cause the formation of peptide YY, cholecystokinin and/or GLP-1 in the intestinal track of said individual to slow the digestive process and to generate satiety.

2. A composition as provided in claim 1 in which said composition is packaged in a time release package to facilitate continuous maintenance of nutrients in the gastrointestinal tract of said individual.

3. A dietary composition as recited in claim 1 in which said composition comprises egg white and unsaturated fat.

4. A dietary composition as recited in claim 1 in which said fat is derived from one or more of the following oils: olive oil, fish oil, flax seed oil, and hemp oil.

5. A dietary composition as recited in claim 1 in which said composition comprises not less than 250 calories derived from protein.

6. A dietary composition as recited in claim 5 in which said composition comprises not less than 400 calories of fat.

7. A dietary composition as recited in claim 1 in which said composition comprises protein having not less than 230 calories and fat having not less than 400 calories, said daily composition having less than a total calorie count of 1000 calories.

8. A dietary composition as recited in claim 1 in which said daily composition is pre-packaged in not less than 8 serving containers for consumption at regular intervals throughout the day.

9. A dietary composition as recited in claim 1 in which said daily composition is a liquid and is pre-packaged in not less than 8 small containers for consumption throughout the day to maintain the presence of macronutrients in the gastrointestinal tract throughout the day.

* * * * *